(12) United States Patent
Ho

(10) Patent No.: US 9,320,865 B2
(45) Date of Patent: Apr. 26, 2016

(54) SUPER-SOFT GEL SEAL AND MASK USING SAME

(75) Inventor: Peter Chi Fai Ho, Pittsburgh, PA (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 2292 days.

(21) Appl. No.: 11/715,760

(22) Filed: Mar. 8, 2007

(65) Prior Publication Data

US 2007/0221227 A1    Sep. 27, 2007

Related U.S. Application Data

(60) Provisional application No. 60/780,589, filed on Mar. 9, 2006.

(51) Int. Cl.
*A61M 16/06* (2006.01)

(52) U.S. Cl.
CPC .......... *A61M 16/06* (2013.01); *A61M 16/0633* (2014.02)

(58) Field of Classification Search
CPC ....... A61M 16/06–16/0655; A61M 2016/0661
USPC ............... 128/206.24, 857, 858, 863, 200.24,
128/201.22, 201.23, 202.18, 205.25,
128/206.11, 206.21, 206.23, 206.27, 206.28
See application file for complete search history.

(56) References Cited

U.S. PATENT DOCUMENTS

| | | |
|---|---|---|
| 2,254,854 A | 9/1941 | O'Connell |
| 2,931,356 A | 4/1960 | Schwarz |
| 5,181,506 A | 1/1993 | Tardiff, Jr. |
| 5,607,167 A | 3/1997 | Franckx |
| 5,647,357 A | 7/1997 | Barnett et al. |
| 5,665,809 A | 9/1997 | Wojtowicz |
| 5,884,624 A | 3/1999 | Barnett et al. |
| 6,019,101 A | 2/2000 | Cotner et al. |
| 6,029,842 A | 2/2000 | Sheffler et al. |
| 6,070,579 A * | 6/2000 | Bryant et al. ............ 128/207.11 |
| 6,082,360 A * | 7/2000 | Rudolph et al. ......... 128/206.25 |
| 6,176,239 B1 * | 1/2001 | Grove et al. ............ 128/206.24 |
| 6,397,847 B1 | 6/2002 | Scarberry et al. |
| 6,631,718 B1 | 10/2003 | Lovell |
| 6,796,308 B2 | 9/2004 | Gunaratnam et al. |
| 6,895,965 B2 | 5/2005 | Scarberry et al. |
| 7,216,647 B2 * | 5/2007 | Lang et al. ............... 128/206.24 |
| 7,353,827 B2 * | 4/2008 | Geist ........................ 128/207.11 |

(Continued)

FOREIGN PATENT DOCUMENTS

| | | |
|---|---|---|
| FR | 2 658 725 | 8/1991 |
| FR | 2 749 176 | 12/1997 |
| WO | WO 00/74758 | 12/2000 |

OTHER PUBLICATIONS

Stewart et al., "Wheelchair Cushion Effect on Skin Temperature, Heat Flux, and Relative Humidity", Arch Phys Med Rehabil, May 1980, pp. 229-233, vol. 61.

(Continued)

*Primary Examiner* — Steven Douglas
*Assistant Examiner* — LeToya M Louis
(74) *Attorney, Agent, or Firm* — Michael W. Haas

(57) ABSTRACT

A seal that contacts a portion of a patient to provide a comfortable interface between an external device, such as a respiratory mask, and the patient. The seal includes an elastic casing filled with a soft gel substance having a cone penetration of from about 5 to 200 penetrations.

1 Claim, 14 Drawing Sheets

(56) References Cited

U.S. PATENT DOCUMENTS

| | | |
|---|---|---|
| 2002/0166691 A1 | 11/2002 | Yaworski et al. |
| 2003/0104160 A1 | 6/2003 | Roosen et al. |
| 2004/0025883 A1 | 2/2004 | Eaton et al. |
| 2004/0045551 A1 | 3/2004 | Eaton et al. |
| 2004/0118406 A1 | 6/2004 | Lithgow et al. |
| 2004/0211428 A1* | 10/2004 | Jones et al. .............. 128/206.27 |
| 2005/0022818 A1 | 2/2005 | Kwok et al. |
| 2005/0199239 A1* | 9/2005 | Lang et al. ............... 128/206.24 |
| 2005/0250903 A1* | 11/2005 | Tanaka et al. ................. 524/861 |
| 2006/0237017 A1* | 10/2006 | Davidson et al. ........ 128/205.25 |
| 2006/0283456 A1* | 12/2006 | Geiselhart et al. ....... 128/206.24 |

OTHER PUBLICATIONS

PCT Search Report and Written Opinion, Dec. 7, 2007.
Global Engineering Documents, "Standard Test Method for Cone Penetration of Lubricating Grease Using One-Quarter and One-Half Scale Cone Equipment", American Society for Testing and Materials.
GLS Corporation, "Ultrasoft TPEs March Forward", Injection Molding Magazine, Jul. 2003.

* cited by examiner

SUPER-SOFT GEL SEAL AND MASK USING SAME

CROSS-REFERENCE TO RELATED APPLICATIONS

This application claims priority under 35 U.S.C. §119(e) from provisional U.S. patent application No. 60/780,589 filed Mar. 9, 2006, the contents of which are incorporated herein by reference.

BACKGROUND OF THE INVENTION

1. Field of the Invention

The present invention pertains to a seal that contacts a portion of a patient to provide a comfortable interface between an external device, such as a respiratory mask, and the patient. Specifically, the present invention pertains to a seal having an elastic casing filled with a soft gel substance. The present invention also pertains to a respiratory mask having such a seal and to a method of interfacing a patient with an external device, such as a respiratory mask, using such a seal.

2. Description of Related Art

A variety of respiratory masks are known having a flexible seal that covers the areas surrounding the nose and/or mouth of a human user and that are designed to create a continuous seal against the user's face. Because of the sealing effect created, gases can be provided at a positive pressure within the mask for consumption by the user. The uses for such masks range from high altitude breathing (aviation applications), swimming, mining, and fire fighting applications and various medical diagnostic and therapeutic applications.

One requisite of many of these masks, particularly medical respiratory masks, is that they provide an effective seal against the user's face to prevent leakage of the gas being supplied. Commonly, in conventional mask configurations, a good mask-to-face seal has been attained in many instances only with considerable discomfort for the user. This problem is most crucial in those applications, especially medical applications, which require the user to wear the mask continuously for hours or perhaps even days. In such situations, the user will not tolerate the mask for long durations and optimum therapeutic or diagnostic objectives will not be achieved, or will be achieved with great difficulty and considerable user discomfort.

Several types of respiratory masks for the types of applications mentioned above are known. Perhaps the most common type of mask incorporates a smooth sealing surface extending around the periphery of the mask and exhibiting a generally uniform, i.e., predetermined or fixed, seal surface contour that is intended to be effective to seal against the user's face when force is applied to the mask with the sealing surface in confronting engagement with the user's face. The sealing surface typically consists of an air or fluid filled cushion, or it may simply be a molded or formed surface of a resilient seal element made of an elastomer such as plastic, rubber, silicone, vinyl or foam.

Such masks have performed well when the fit is good between the contours of the seal surface and the corresponding contours of the user's face. This may occur, for example, if the contours of the user's face happen to match well with the predetermined contours of the seal. However, if the seal fit is not good, there will be gaps in the seal-to-face interface resulting in gas leaking from the mask at the gaps. Excessive force will be required to compress the seal member to close the gaps and attain a satisfactory seal in those areas where the gaps occur. Such excessive force is unacceptable because it produces high pressure points elsewhere on the face of the user where the mask seal contour is forcibly deformed against the face to conform to the user's facial contours. This will produce considerable user discomfort and possible skin irritation and breakdown anywhere the applied force exceeds the local perfusion pressure, which is the pressure that is sufficient to cut off surface blood flow. Ideally, contact forces should be limited between the mask and the user's face to avoid exceeding the local perfusion pressure, even at points where the mask seal must deform considerably.

The problem of seal contact force exceeding desirable limits is even more pronounced when the positive pressure of the gas being supplied is relatively high or is cyclical to relatively high levels. Because the mask seals by virtue of confronting contact between the mask seal and the user's face, the mask must be held against the face with a force sufficient to seal against leakage of the peak pressure of the supplied gas. Thus, for conventional masks, when the supply pressure is high, headstraps or other mask restraints must be relatively tightly fastened. This produces high localized pressure on the face, not only in the zone of the mask seal, but at various locations along the extent of the retention straps as well. This, too, will result in discomfort for the user after only a brief time. Even in the absence of excessive localized pressure points, the tight mask and headstraps may become extremely uncomfortable, and user discomfort may well cause discontinued cooperation with the treatment regimen. Examples of respiratory masks possessing continuous cushion sealing characteristics of the type just described are provided in U.S. Pat. Nos. 2,254,854 and 2,931,356.

U.S. Pat. No. 5,181,506 describes a protective gas mask for military applications. The mask includes a three-layer face piece, the central layer of which is a thick layer of relatively stiff material having preformed V-shaped channels. The channels are "overfilled" with a gel or both gel and compressed air to create bulges in an inner face-contacting layer that are adapted to seal against the contours of a user's face. The inherent stiffness of the central layer in combination with the structural rigidity provided by the V-shaped channels, especially when overfilled with gel/air, results in a comparatively unyielding facial seal. Indeed, the mask is deployed in combination with a tightly fitting hood in order to draw the face piece firmly against the user's head to generate the desired facial seal. As will be appreciated, the comfort afforded such a construction is quite limited and certainly not appropriate for those applications, such as respiratory therapy situations, where a user must occasionally wear a mask for prolonged periods of time.

Several classes of cushion materials, including gels and foams, were analyzed in a study by S. F. C. Stewart, V. Palmieri and G. V. B. Cochran, *Arch. Phys. Med. Rehabil.*, Vol. 61, (May 1980). That study compared the relative advantages and disadvantages of such cushion materials when used as wheelchair cushions, specifically the effects of such materials on skin temperature, heat flux, and relative humidity at the skin-cushion interface. Each of these factors, along with applied pressure in excess of local perfusion pressure, has been identified as a contributor to breakdown of skin tissue at the skin-cushion interface.

In that study, foam cushions were reported to increase skin temperatures by several degrees after a few hours of use. This was suggested to be a result of the comparatively low heat flux characteristics of foam materials. That is, the foam materials and the air entrapped within them tend to be poor conductors of heat. Conversely, gel pads, as a group, showed a considerably higher heat flux than foam, sufficient, in fact, to maintain skin temperatures relatively constant after several hours of use. The sole benefit of foam versus gel reported in the study was that foams produced lesser relative humidity than gels at the skin-cushion interface. This was attributed to the open cell structure of the foams which provide a pathway through which moisture can diffuse. This seeming advantage is somewhat problematic, however, in that open cell foam tends to promote bacteria growth when exposed to perspiration. Bacteria, in turn, contaminate the foam thereby considerably hindering its useful service life.

Moreover, whether air, fluid or, in the case of U.S. Pat. No. 5,181,506, gel filled, or whether formed as an elastomer such as foam, plastic, rubber, silicone and the like, the resiliency or recoil characteristics of presently available cushion type respiratory mask seals have not been well suited to form an effective seal with the topography of the user's face in the absence of considerable headstrap tensile forces.

A respiratory mask facial seal comprising a seal cushion formed of a gel substance is disclosed in U.S. Pat. Nos. 5,647,357 and 5,884,624, the disclosures of which are herein incorporated by reference. The gel substance is a viscoelastic polyurethane polymer possessing resilience or recoil characteristics corresponding substantially to those of human fat tissue. Specifically, the seal cushion has a resiliency, as defined by durometer measured on the Shore 00 scale which is used to gauge the resiliency of very soft resilient materials, of about 10 or softer and, most preferably, about 0. Such resiliency corresponds substantially to that of human fat tissue which also exhibits a durometer reading of 0 on a Shore 00 scale. More specifically, the seal cushion exhibits a resiliency or durometer on the Shore 000 scale (which scale is used to measure the resiliency of extremely soft resilient materials) of about 20 to about 45. By comparison, human fat tissue registers a durometer of about 10 on the Shore 000 scale. In one embodiment, the gel substance is covered by a flexible plastic film.

A customizable seal that contacts a portion of a patient is disclosed in U.S. Pat. Nos. 6,397,847 and 6,895,965, the disclosures of which are herein incorporated by reference. The customizable seal, in a preferred embodiment, has a first portion fabricated from a gel substance having the recoil characteristic analogous to that of human fat, as disclosed in U.S. Pat. Nos. 5,647,357 and 5,884,624. The seal has a second portion associated with the first portion and including a selectively formable substance adapted to be molded from a first pattern into a second pattern and to retain the second pattern responsive to being so molded.

Some of the known conventional gel masks discussed above include a non-elastic casing encapsulating a gel substance. The casing is formed from a polyurethane which has a typical hardness of 75 Shore A and 80-250% elongation. This non-elastic casing is thermal formed from very thin film (approximately 2 to 10 mils thick). The forming capability of such a thin film limits the complexity of the geometry and the wall thickness distribution. Also, because of the thinness of the film, the encapsulation provides no structural function. The gel substance, therefore, has to provide the form and structure for the seal and is relatively hard (ranging from 20 to 25 Shore 00).

SUMMARY OF THE INVENTION

Accordingly, it is an object of the present invention to provide a seal adapted for confronting engagement with a surface of a user to form a sealed interface therewith that overcomes the shortcomings of conventional seal techniques. This object is achieved, according to one embodiment of the present invention, by providing a seal including an elastic casing filled with a soft gel substance. In one embodiment of the present invention, the soft gel is preferably a super soft silicone gel having a cone penetration of from 5 to 200 penetrations. The soft gel substance, however, is not limited to silicone but can be any soft gel, for example a polyurethane gel, having the physical properties of cone penetration of from 5 to 200 penetrations. The elastic casing carries the structure of the form of the seal so that the gel substance can be more fluid and softer than conventional gel substances. The seal of the present invention provides a more effective seal, increased body tissue compatibility, higher conformability, and a more comfortable interface than conventional gel mask seals.

It is a further object of the present invention to provide a respiratory mask using a seal including an elastic casing filled with a soft gel substance. This object is achieved by providing a respiratory mask that includes a relatively rigid mask body having a first opening and a second opening defined therein. A seal is operatively connected to the mask body and adapted for confronting engagement with a surface of a user to form a sealed interface therewith. This object is further achieved by providing a system using a respiratory mask and a seal including an elastic casing filled with a soft gel substance.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", an and "the" include plural referents unless the context clearly dictates otherwise.

DETAILED DESCRIPTION OF THE EXEMPLARY EMBODIMENTS

Figure 1:
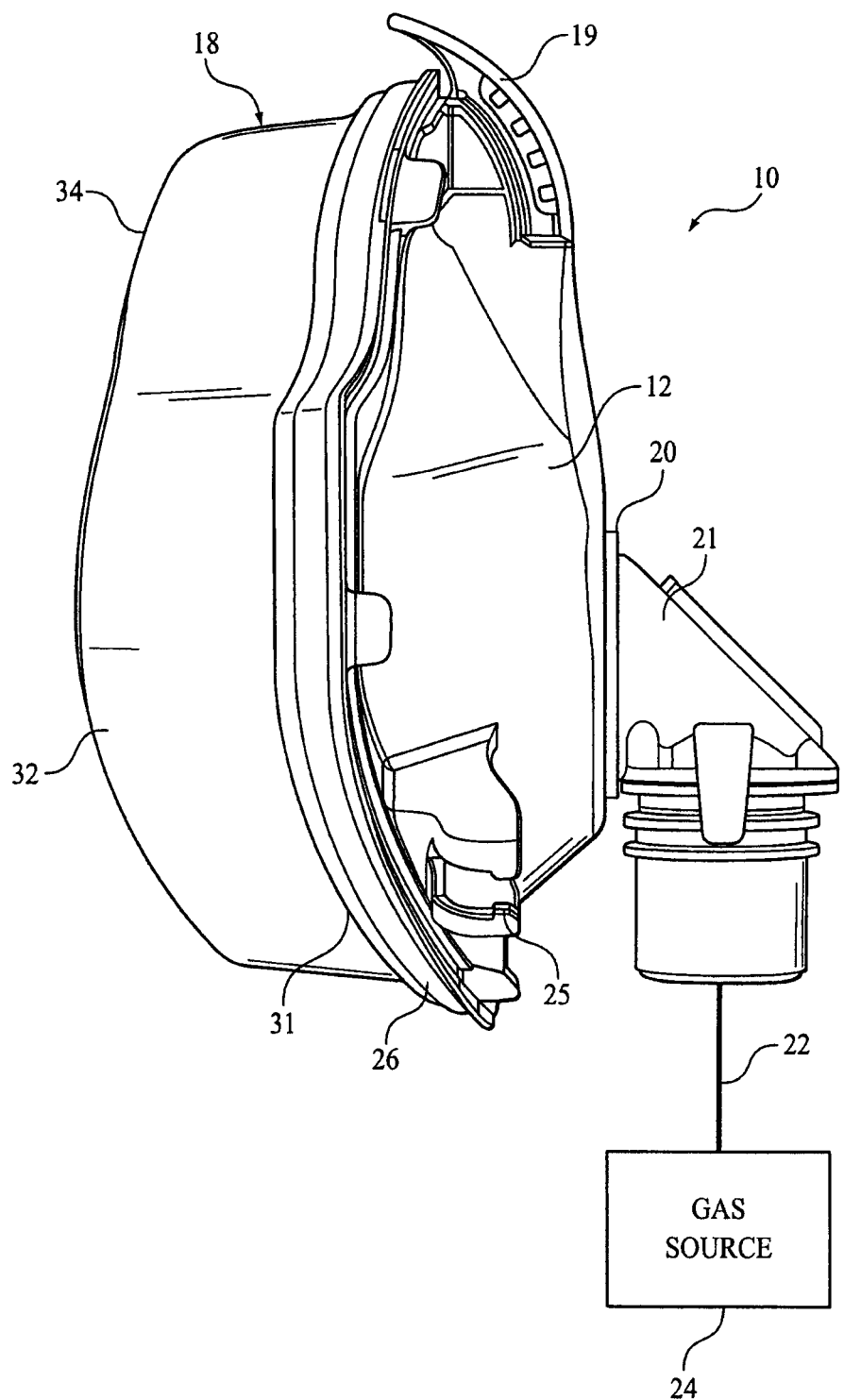
FIG. 1 is a side elevation view of a respiratory mask of a first embodiment according to the present invention, the respiratory mask being schematically depicted in communication with a source of respiratory gas.

Directional phrases used herein, such as, for example, horizontal, vertical, left, right, clockwise, counterclockwise, top, bottom, up, down, front, rear, and derivatives thereof, relate to the orientation of the elements shown in the accompanying drawings and are not limiting upon the claims unless expressly recited therein. Furthermore, the term "outer-side" or "front", and all derivatives thereof, refer, for example, to the end of a respiratory mask that is nearest the patient when the respiratory mask is donned by the patient. In contrast, the term "patient-side" or "rear" and all derivatives thereof refer, for example, to the end of the respiratory mask that is farthest away from the patient when the respiratory mask is donned by the patient.

As employed herein, the term "number" shall mean one or more than one and the singular form of "a", "an", and "the" include plural referents unless the context clearly indicates otherwise. Additionally as employed herein, the statement that two or more parts are "connected" or "coupled" together shall mean that the parts are joined together either directly or joined together through one or more intermediate parts, whereas the statement that two or more parts are "attached" or "affixed" shall mean that the parts are joined together directly.

Referring to FIGS. 1-5, there is generally indicated at 10, a respiratory mask according to a first exemplary embodiment including a body or shell 12 having an open side 14 that defines a generally annular surface 16 to which is sealingly coupled a seal 18 constructed according to a first embodiment of the instant invention. Shell 12 is preferably, although not necessarily, a generally rigid shell, whereas seal 18, in the illustrated embodiment, is a flexible, resilient member that will be described in greater detail hereinafter.

Shell 12 also defines an opening 20 to which, in the illustrated embodiment, there is connected a fluid coupling device, such as a swivel coupling 21 for carrying fluid, such as a breathing gas, between the chamber within the mask and an external gas source. It is to be understood that the present invention contemplates a variety of fluid coupling devices be attachable, either permanently or selectively, to opening 20 to carry fluid to or from the chamber defined by mask 10. In the illustrated embodiment, opening 20 and intervening coupling 21 connect mask 10 via a conduit, which is represented by dashed line 22, to a source of gas 24, e.g., a blower or other suitable device, for providing a flow of pressurized breathing gas, for example, for administration of the gas to a user. Coupling 21 preferably includes exhaust vents 23 which exhaust exhaled gases in a known manner. In this embodiment, seal 18 is preferably attached to shell 12 using ring 26 in a known manner.

Source of gas 24 is any device that provides gas to the user. The gas source may include an oxygen supply, a ventilator, a pressure support device, such as a CPAP device, a variable pressure device, e.g., a BiPAP®, Bi-Flex, or C-Flex device manufactured and distributed by Respironics, Inc. of Pittsburgh, Pa., or an auto-titration pressure support system. A BiPAP, Bi-Flex, or C-Flex device is a pressure support device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea, hypopnea, flow limited breathing, upper airway resistance, or snoring.

The mask shown is a full or an oral/nasal mask that accommodates both the mouth and nasal regions of the user's face. It is to be understood, however, that the present invention also contemplates a nasal mask that accommodates both the nasal regions of a user or a total face mask that accommodates substantially the entire facial area of the patient. It should also be understood that the illustrated embodiments are examples only of masks using the elastic casing and soft gel of the present invention and that the present invention is not limited to the embodiments described herein.

In the illustrated embodiment, the lower corners of mask shell 12 also include headgear attaching elements in the form of receiving socket attachment elements 25 which cooperate with corresponding ball elements (not illustrated) on headgear straps. The ball and socket configuration, and other headgear attachment configurations suitable for use with the present invention, are disclosed in co-pending U.S. patent application Ser. No. 10/629,366, (publication no. US-2004-0025883-A1) the contents of which are incorporated herein by reference. It is to be understood, however, that the present invention contemplates using any conventional connection assemblies to attach a headgear to mask shell 12 in this or any of the other embodiments.

The present invention contemplates the headgear (not illustrated) that can be used with mask 10 can be any suitable headgear, i.e., any conventional headgear used in the patient interface field. For example, a typical headgear assembly comprises a headpiece that overlies a portion of the patient's crania and with headgear straps extending therefrom to adjustably connect the headgear to the mask.

Figure 2:
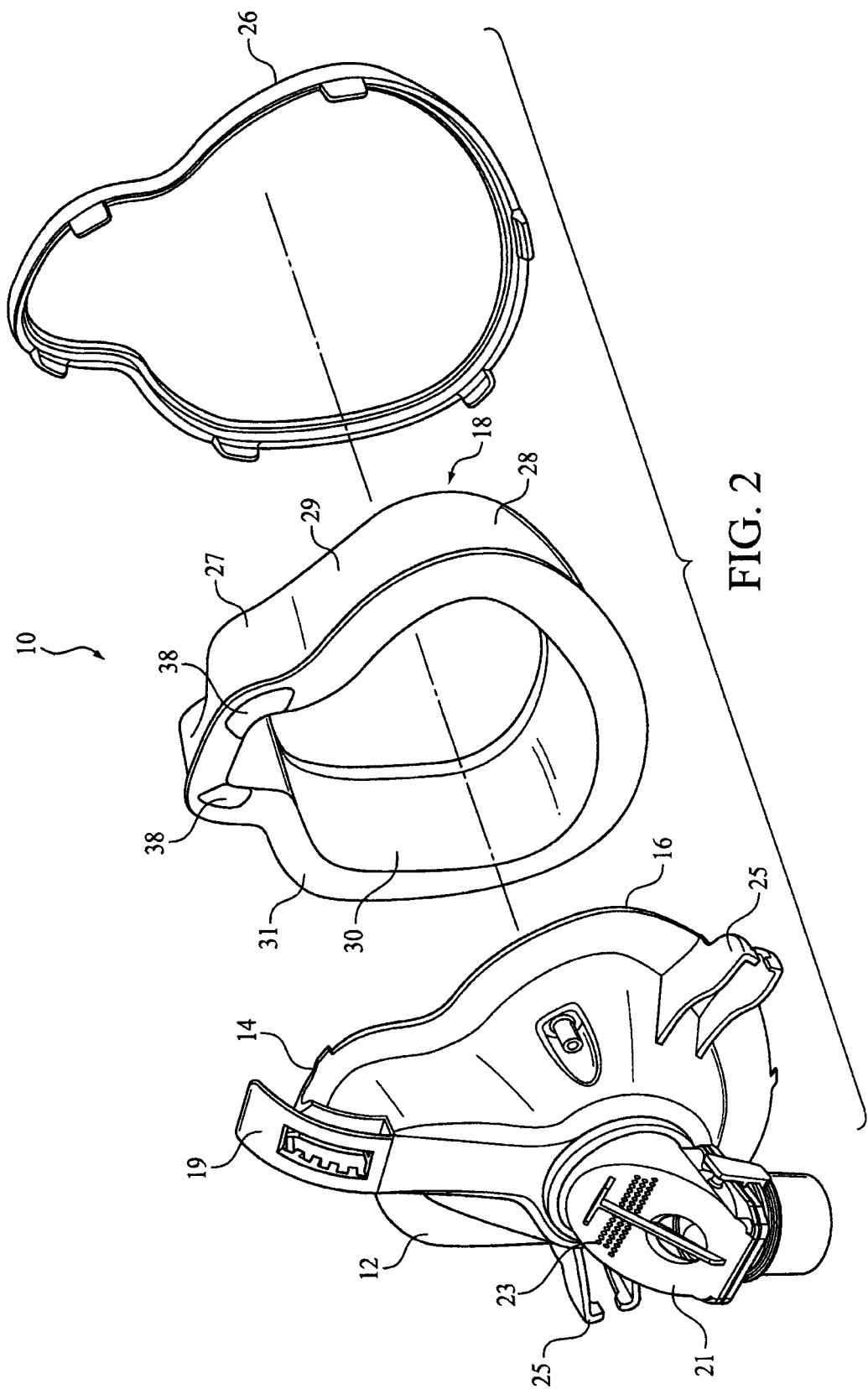
FIG. 2 is an exploded view of the respiratory mask of FIG. 1.
Figure 3:
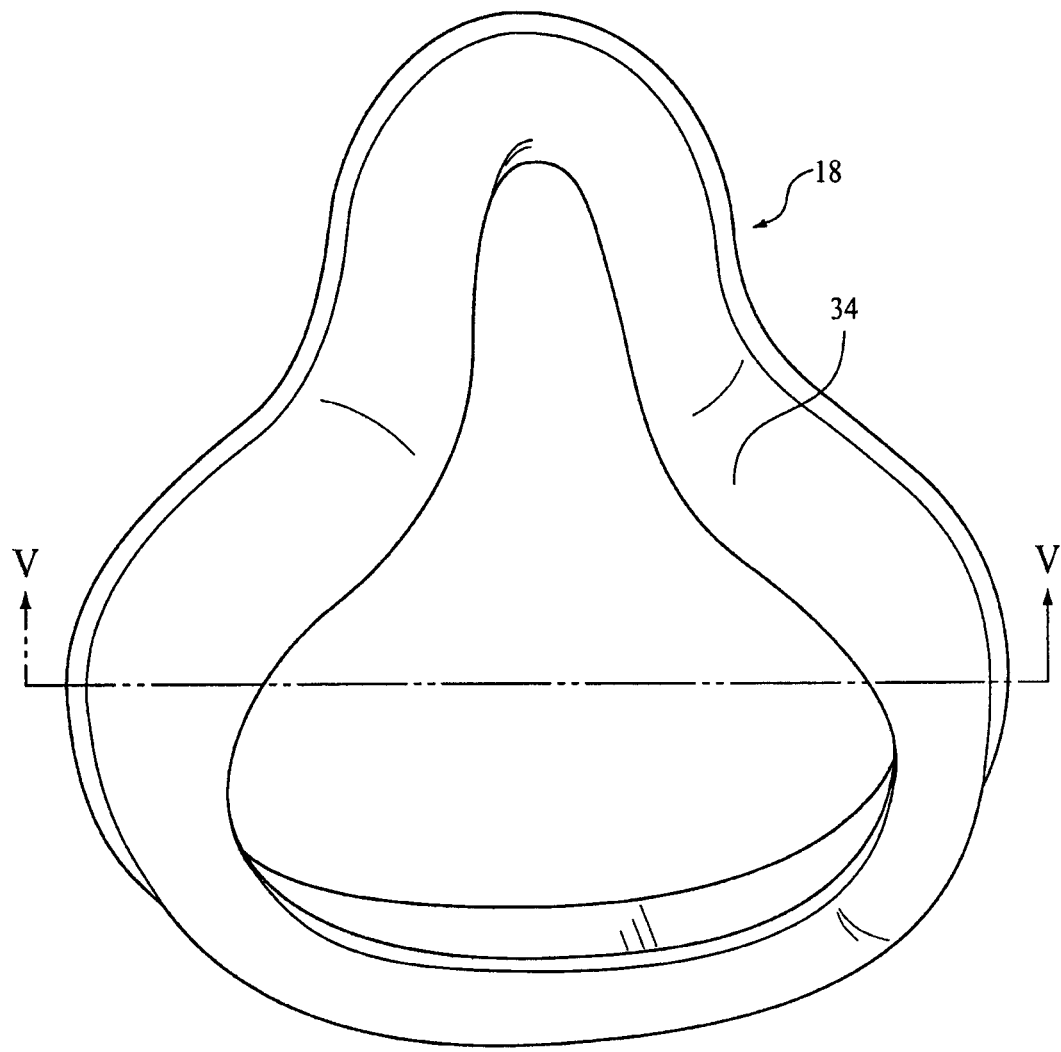
FIG. 3 is a front view of a seal of the respiratory mask of FIG. 1.
Figure 4:
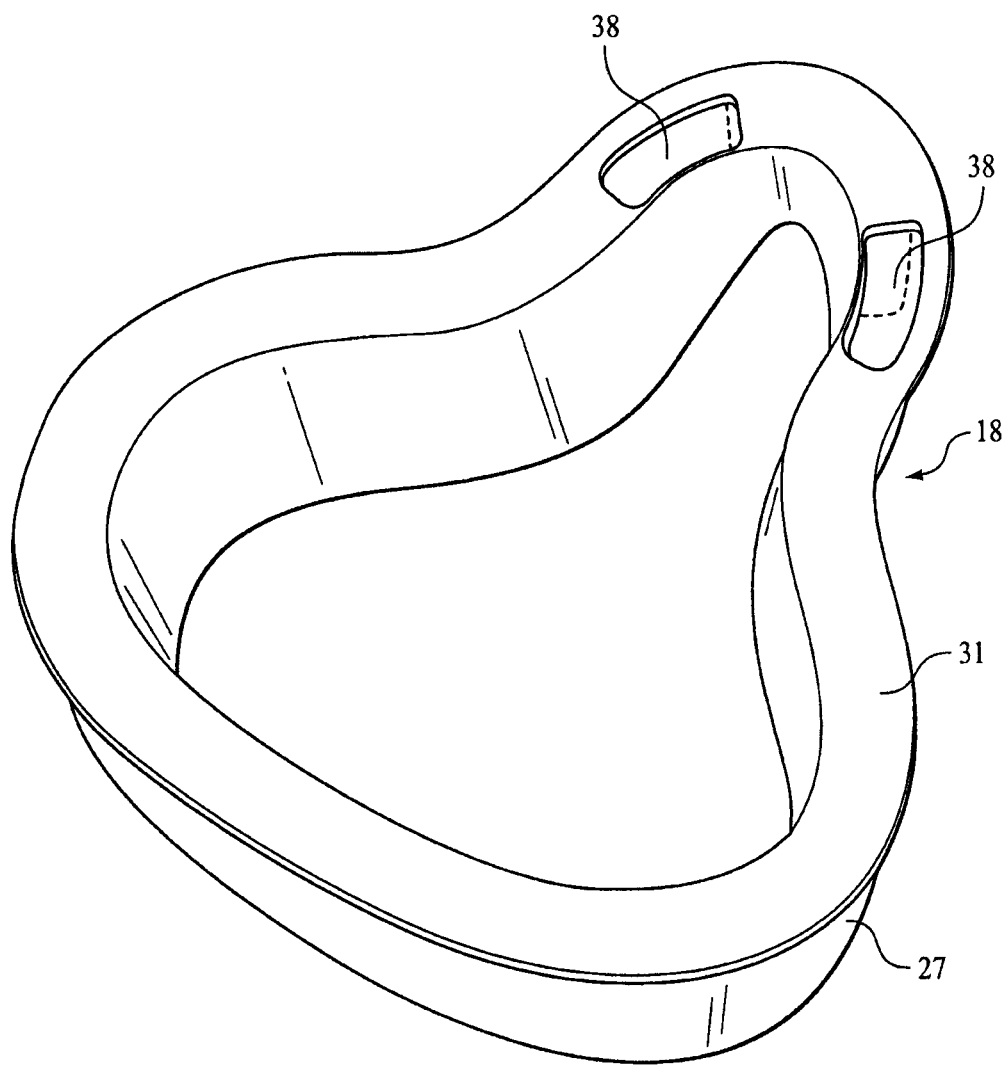
FIG. 4 is a rear perspective view of a seal of the respiratory mask of FIG. 1.
Figure 5:
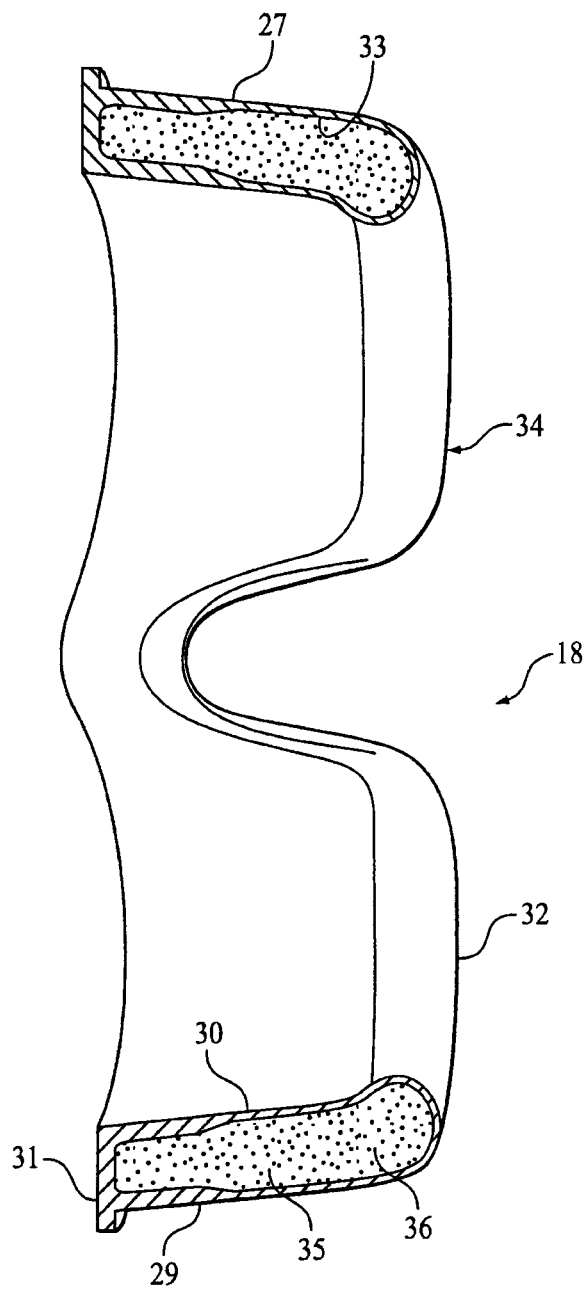
FIG. 5 is a cross-sectional view of the seal taken along line V-V of FIG. 3.

It should be further noted that respiratory mask 10 illustrated in the FIGS. 1 and 2 is shown without a forehead support. In the actual mask, a forehead support attaches to mask shell 12 at attachment member 19 so that the forehead support is moveable relative to the mask shell. An example of a mask having a forehead support suitable for use in the present invention is described in U.S. patent application Ser. No. 10/654,379 (publication no. US-2004-0045551-A1) the contents of which are incorporated herein by reference. It is to be understood that the present invention contemplates using any type or configuration of forehead support (or none at all) in combination with mask shell 12, including a forehead support that is fixed (not adjustable) relative to the mask shell.

Seal 18 in the illustrated embodiments includes an elastic casing 27 comprising and annular member 28 including a peripheral wall portion 29 and an interior wall portion 30 having a generally annular base or inner end 31 configured so as to substantially match surface 16 of shell 12 to which it is attached. Peripheral wall portion 29 further establishes an outer end 32 generally opposite inner end 31. Outer end 32 defines a generally annular contoured sealing surface 34 adapted for confronting, sealing engagement with a user's face. As will be more fully developed later herein, in the illustrated embodiment, the contour of sealing surface 34 is preformed to closely approximate the surface contour of a user's facial structure, especially in the areas of the bridge of the nose, the cheeks adjacent the nose, the user's chin area, and the intervening areas contiguous to these.

It is to be understood that the contour of sealing surface 34 can have alternative configurations depending on the type of mask to which the seal is attached. For a nasal mask (not illustrated), for example, sealing surface 34 is contoured to accommodate the area intermediate the nose and upper lip in lieu of the user's chin. In either case, variation in the user's facial structure, especially in the area of the bridge of the nose, for example, makes considerable seal flexibility necessary to accommodate the many different facial contours likely to be encountered.

In accordance with the embodiment of the present invention illustrated in FIGS. 1-5, elastic casing 27 includes an interior chamber 35 formed between peripheral wall portion 29 and interior wall portion 30. Casing 27 is preferably precision molded in an elastic material such as Liquid Injection Molded (LIM) silicone rubber or in another elastic material such as Thermal Plastic Elastomer (TPE). Interior chamber 35 of casing 27 is filled with a gel substance 36, such as a super soft silicone gel. The soft gel substance, however, is not limited to silicone but can be any soft gel, for example a polyurethane gel, having the physical properties discussed below. The gel substance is then allowed to cure or cross-link at room temperature or with heat. Depending on the gel substance used, cross-linking (or curing) of the gel substance may be complete or partial. Alternatively, a non-cross-linked gel substance can be used in some extremely soft applications.

The elastic property of the material of casing 27 reduces the restriction of gel substance 36 encapsulated inside interior chamber 35 and allows the properties of the gel substance 36 to be exhibited through casing 27. Known conventional gel masks, on the other hand, typically have non-elastic casings which restrict the properties of the gel substance contained therein. Gel substance 36 is generally more flexible and elastic than the material of elastic casing 27. The casing preferably has a minimum elongation of about 400% and a hardness of about 40 Shore A. The material for elastic casing 27 is chosen based on the properties of the gel substance used therewith as will be explained below.

The present invention contemplates that gel substance 36 can be either adhered or not adhered to an interior surface 33 of elastic casing 27. For example, there may be situations where it is desirable to allow the gel substance to move within the elastic casing. Conversely, the present invention contemplate securing gel substance 36 to elastic casing 27, for example, by providing an adhesive between these two elements such as on surface 33 of the elastic casing.

Gel substance 36 preferably has a hardness or stiffness as defined by penetrations measured with a cone penetrometer, which is used to gauge the hardness of extremely soft materials. As is known by those skilled in the art, the cone penetration method is used for materials that are too soft to measure by the Shore 000 scale. The cone penetration method used for measurement of gel stiffness is defined by American Society for Testing and Materials (ASTM) Standard test methods D1403 and D217. Respironics, Inc., the assignee of the present application, developed a test procedure based on ASTM methods D1403 and D217 as described below. More specifically for the gels referred to herein, the test uses the ¼ scale cone size and weight to measure the cone penetration of the gel substance without the casing. The cone penetration measure described in ASTM Standard D 1403 is equivalent to 0.1 mm for each 1 penetration (P). The cone penetration value is determined after a known constant weight is allowed to impart a vertical force, due to gravity alone, upon a sample of the gel.

In accordance with the present invention, the properties of the casing in terms of thickness and resiliency are chosen based on the properties of the gel in terms of hardness or stiffness and resiliency. For example, a thicker and harder casing material would be used with a softer gel than with a harder gel. In other words, gel penetration representing the hardness or stiffness of the gel substance is inversely proportional to the thickness and hardness of the casing. In the following examples, the gel cone penetrations to casing thickness and hardness comparisons apply mainly to the skin contacting area. The casing preferably has different, most likely thicker wall thickness at the base and side areas which are not in direct contact of the patient to provide structural support. For example, referring to FIG. 6A, "t" represents the casing 18 wall thickness at the skin contacting portion, while "b" represents the casing 18 wall thickness at the base of casing 18. "T" represents the encapsulated gel content thickness.

Example (1)

For a gel at cone penetrations of 30 to 50, the encapsulated gel content is about 0.250 inches (6.35 mm) thick while the casing wall thickness is 0.015 inches (0.38 mm) per side and the hardness of the casing is 40 durometer Shore A. For a thicker gel such as 0.500 inches (12.70 mm), the casing wall is thinner at 0.008 inches (0.20 mm) per side. However, the casing wall is preferably 0.015 inches (0.38 mm) per side if a softer casing material such as 20 Shore A is used.

Example (2)

For a gel at cone penetrations of 65 to 100, the encapsulated gel content is about 0.250 inches (6.35 mm) thick while the casing wall thickness is 0.025 inches (0.64 mm) per side and the hardness of the casing is 40 durometer Shore A. For a thicker gel such as 0.500 inches (12.70 mm), the casing wall is thinner at 0.015 inches (0.38 mm) per side. With gel in this penetration range, it is preferable to have a thicker gel content to maximize comfort.

Example (3)

For gel at cone penetrations of 5 to 25, the encapsulated gel content is about 0.250 inches (6.35 mm) thick while the casing wall thickness is 0.010 inches (0.25 mm) per side and the hardness of the casing is 30 durometer Shore A. For a thicker gel such as 0.500 inches (12.70 mm), the casing wall remains the same while the hardness of the casing is decreased to 15 to 20 durometer Shore A to accommodate the increase of the gel thickness. With gel in this penetration range, it is preferable to have a thinner gel content to maximize comfort.

In the above exemplary embodiments of the present invention, gel substance 36 has cone penetrations preferably in the range of 5 to 100. The gel substance may have penetrations as high as 200. The thickness of the gel substance is preferably in the range of 0.250-0.500 inches (6.35-12.70 mm). In the above exemplary embodiments of the present invention, elastic casing 27 preferably has a stiffness of 15-40 durometer Shore A. The thickness of elastic casing 27 preferably is in the range of 0.010-0.025 inches (0.25-0.64 mm).

The preferred resiliency of the gel substance is measured by determining the length of time the gel substance takes to return to substantially its original thickness after being compressed by 50%. Preferably, the resiliency of the gel substance of the present invention has a response time of less than one second. A gel having a response time of less than one second is called a fast respond gel. Fast respond gels are preferred for filling such as gel substance 36. Slow respond gels are gels having a response time of more than one and less than five seconds. Slow respond gels are preferably used for support such as for a forehead pad.

Figure 6A:
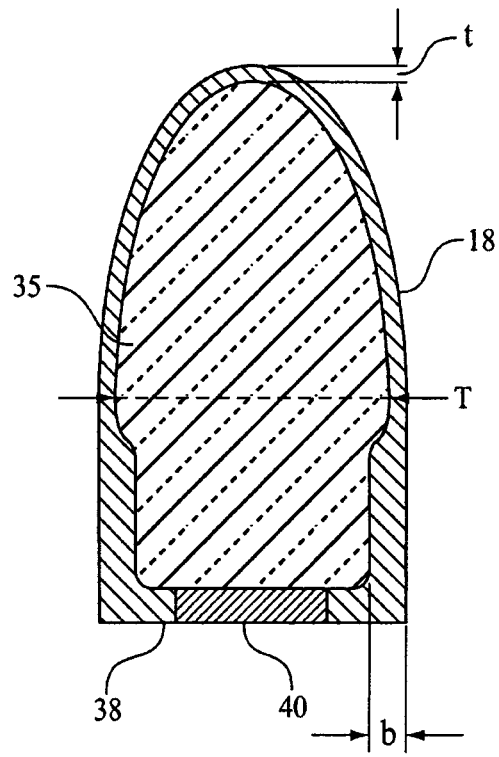
FIGS. 6A and 6B are cross-sectional views of a seal.

Interior chamber 35 (FIG. 5) is closed by inner end 31 which is generally solid having at least one opening 38 (two openings are shown in this illustrated embodiment). Openings 38 are used for filling interior chamber 35 with silicone gel 36 utilizing known filling techniques. Openings 38 may be capped utilizing one of a variety of techniques. In the illustrated embodiment openings are capped with a cap 40 (FIG. 6A).

Figure 7A:
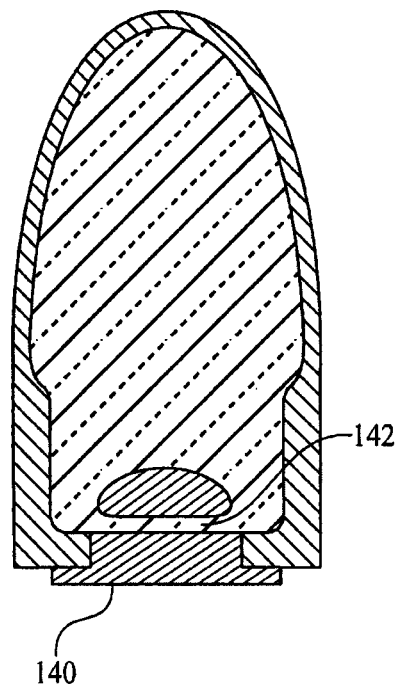
FIG. 7A is a cross-sectional view of a seal.
Figure 7B:
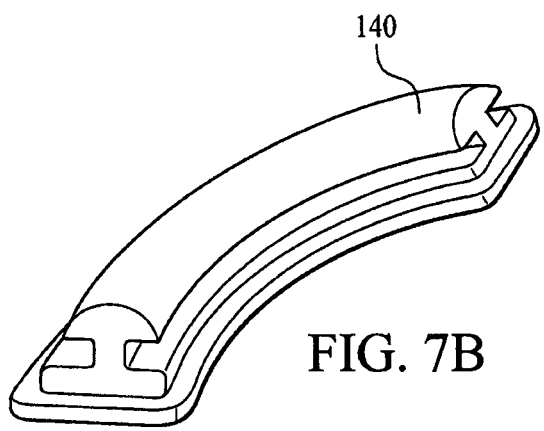
FIGS. 7B and 7C are perspective and partial sections views of the cap of 7A.
Figure 7C:
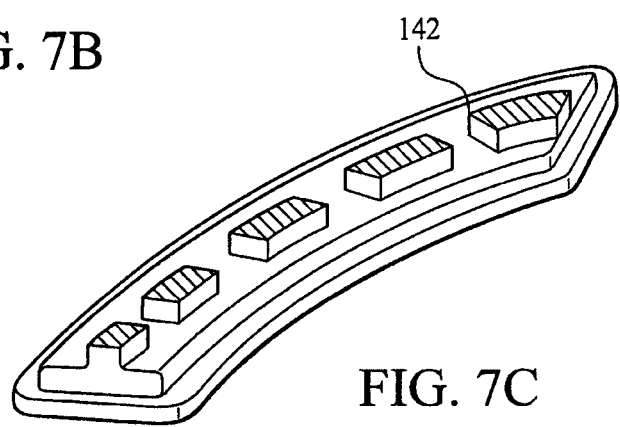

Alternatively, as shown in FIGS. 7A-7C, windows 142 may be preset on each cap 140 to form a mechanical bonding with the gel substance filling windows 142. Alternatively, openings may be sealed with adhesives such a condensation cured Room Temperature Vulcanization (RTV) silicone rubber or heat vulcanized addition cured silicone rubber for a LIM silicone chamber. The sealant used depends on the material used for the chamber. For example, if a TPE is used, solvent bonding is the preferred sealant.

Figure 6B:
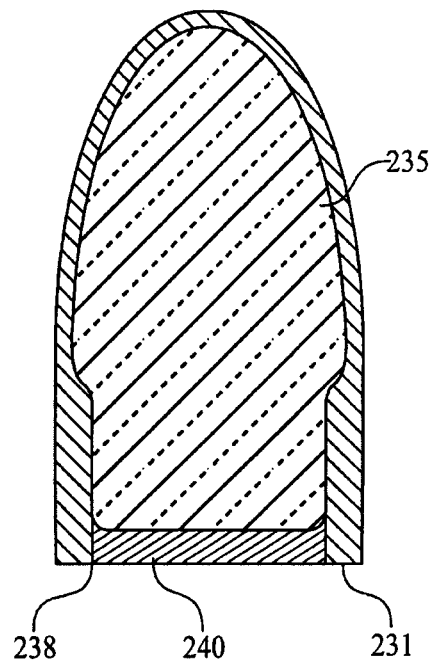
Figure 9:
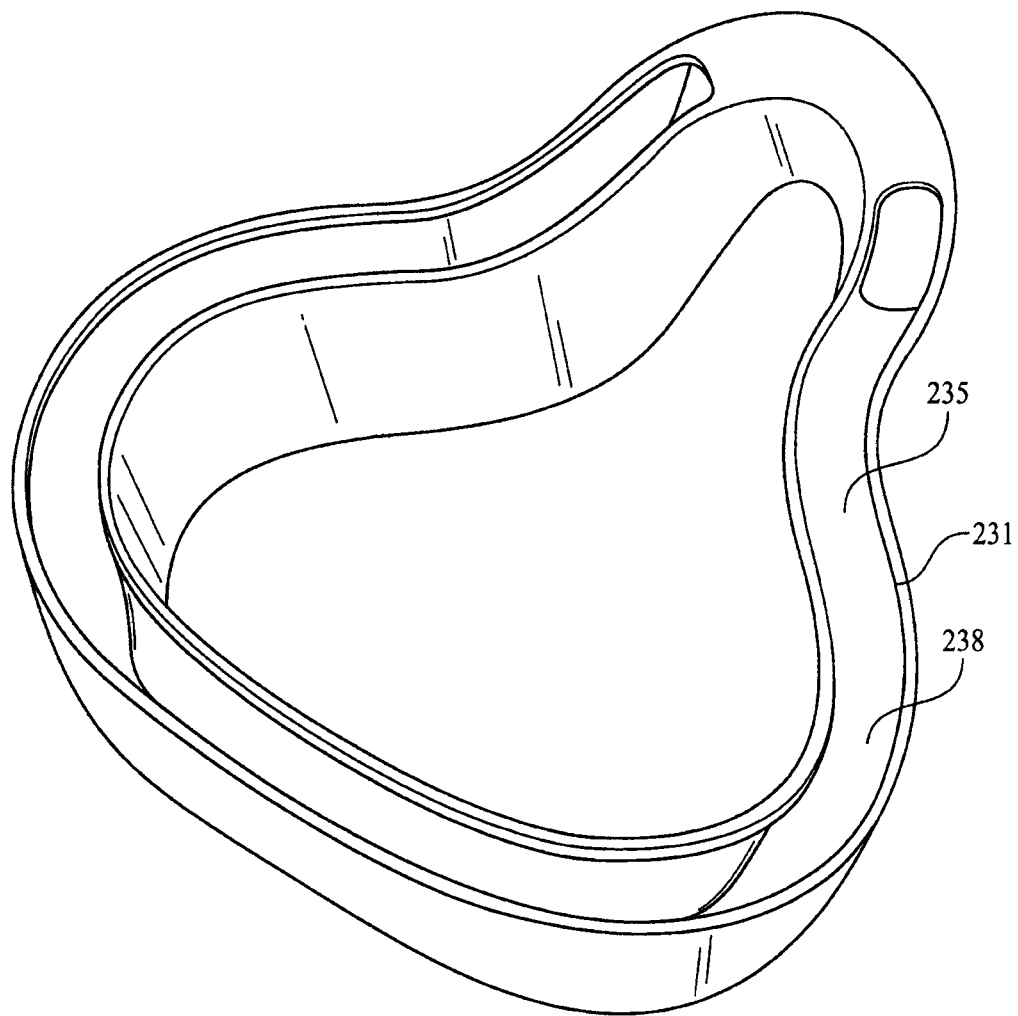
FIG. 9 is a perspective view of a seal according to a further embodiment of the present invention.

An open chamber 235 having an open inner end 231 is illustrated in FIGS. 9 and 6B. Open inner end 231 with an elongated opening 238 may be sealed using sealants similar to those discussed above in reference to openings 38, such as cap 240 shown in FIG. 6B. Also, a matching shaped bottom can be used for a cap.

Figure 8A:
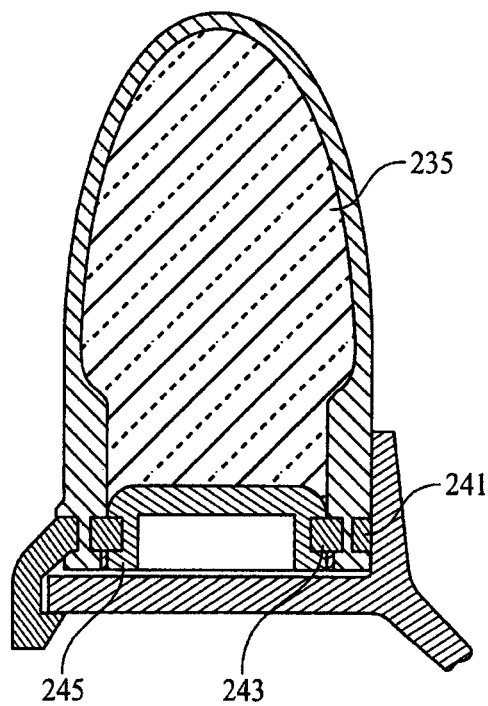
FIGS. 8A and 8B are cross-sectional views of seal embodiments.
Figure 8B:
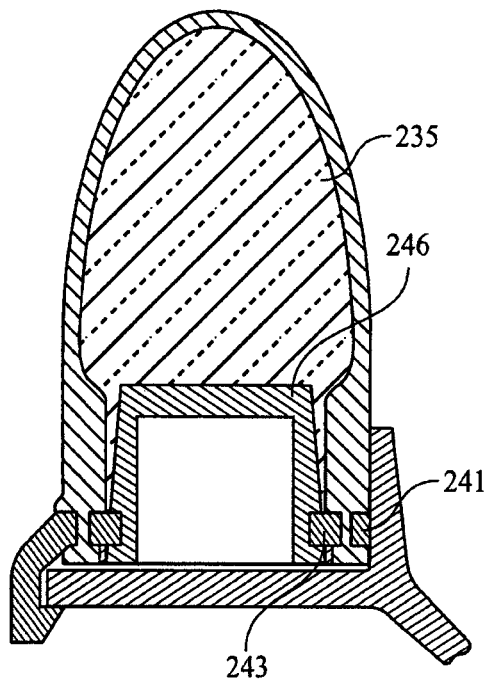

Still yet further embodiments are shown in FIGS. 8A and 8B. An open channel casing is over molded with a substantially more rigid material to form an external ring 241 and an internal ring 243. External ring 241 and internal ring 243 are bonded to more rigid base 245 to completely encapsulate the base of open channel casing to form a casing subassembly. The rings and base may be bonded by gluing, mechanical snap or sonic weld. Casing subassembly is then assembled to mask shell 12. Alternatively, as shown in FIG. 8B, a rigid base 246 may have a deeper profile than rigid base 245 shown in FIG. 8A.

Figure 10:
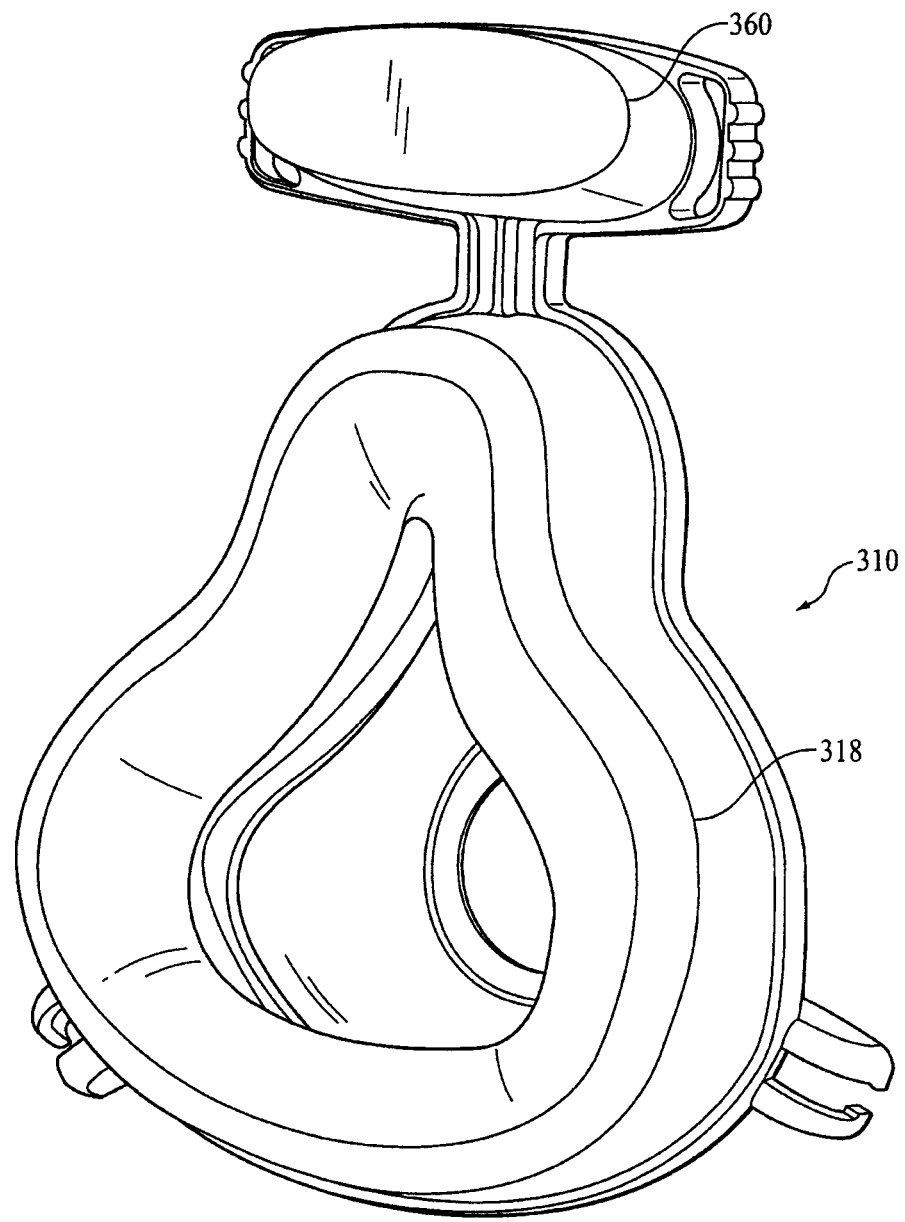
FIG. 10 perspective view of a respiratory mask according to a further embodiment of the present invention.
Figure 11:
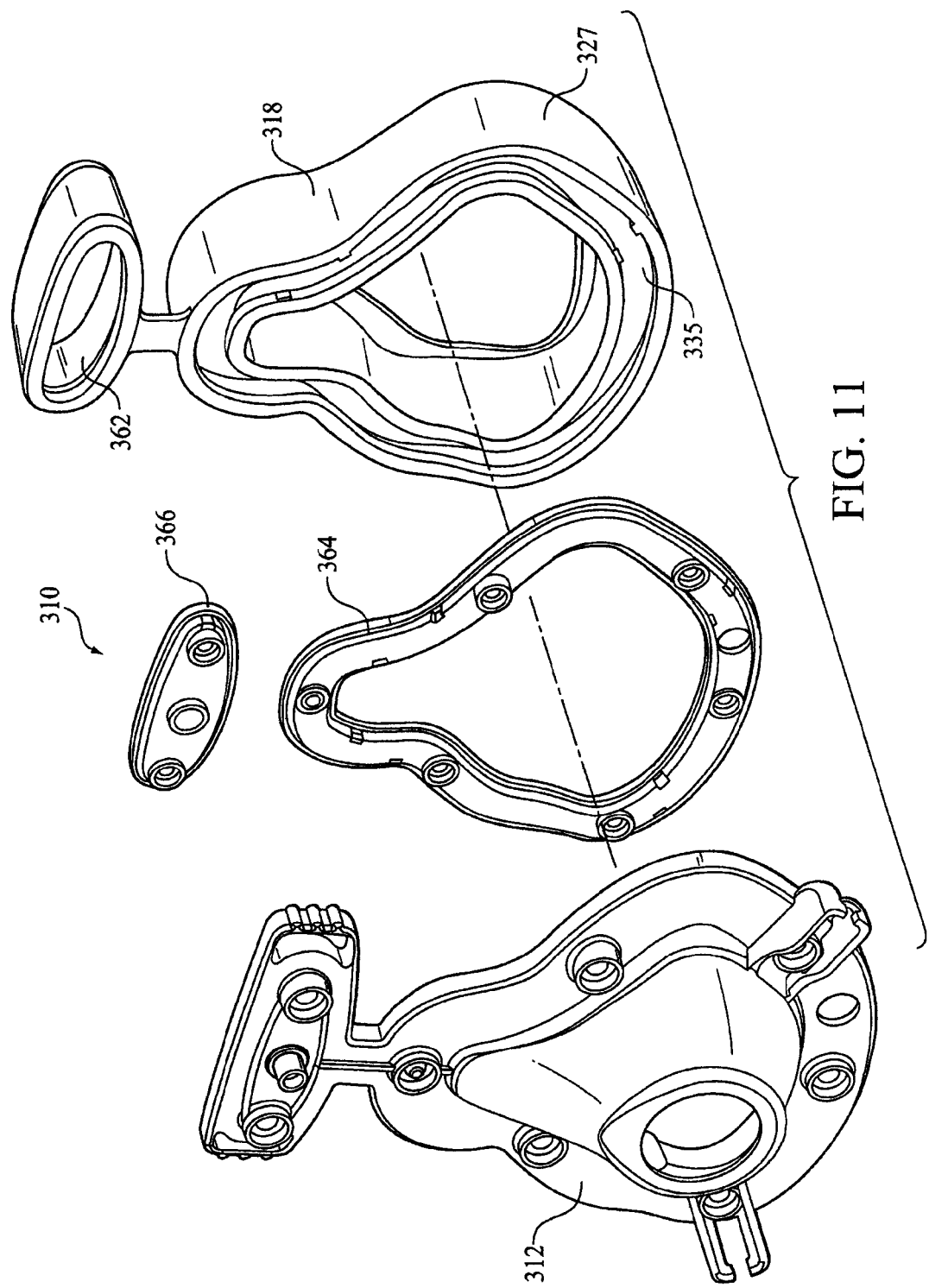
FIG. 11 is an exploded view of the respiratory mask shown in FIG. 10.
Figure 12:
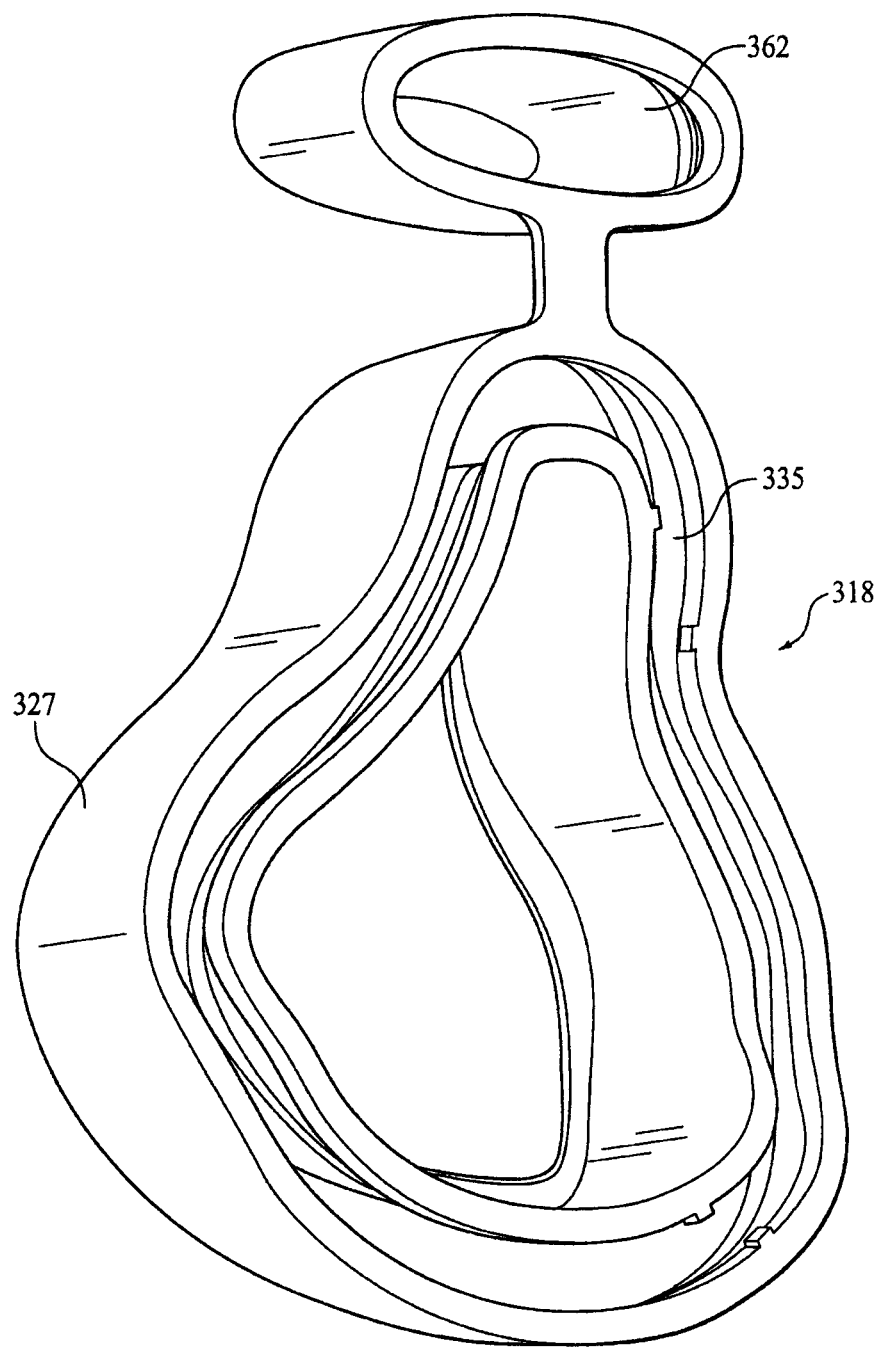
FIG. 12 is a perspective view of a seal according to a further embodiment of the present invention.

An alternative mask 310 is shown in FIGS. 10-12. In this embodiment, a seal 318 includes an integral forehead pad 360. Seal 318 includes a casing 327 having an interior chamber 335 filled with gel substance as well as a forehead chamber 362, also filled with a gel substance. For ease of illustration, the gel substances in the interior chamber of casing 327 and in forehead chamber 362 are not illustrated. The gel substance in forehead chamber 362 is preferably relatively stiffer (having lower penetrations) than the gel substance in casing 327. For example, a forehead pad having a matched contour to the forehead may use a harder gel, while a softer gel may be used for contours which are expected to deform substantially to fit the forehead. Interior chamber 335 and forehead chamber 362 are sealed with a capping ring 364 and forehead cap 366 which also attaches seal 318 to shell 312 by a snap fit but, alternatively, may be attached by other bonding methods such as gluing or welding.

Figure 13:
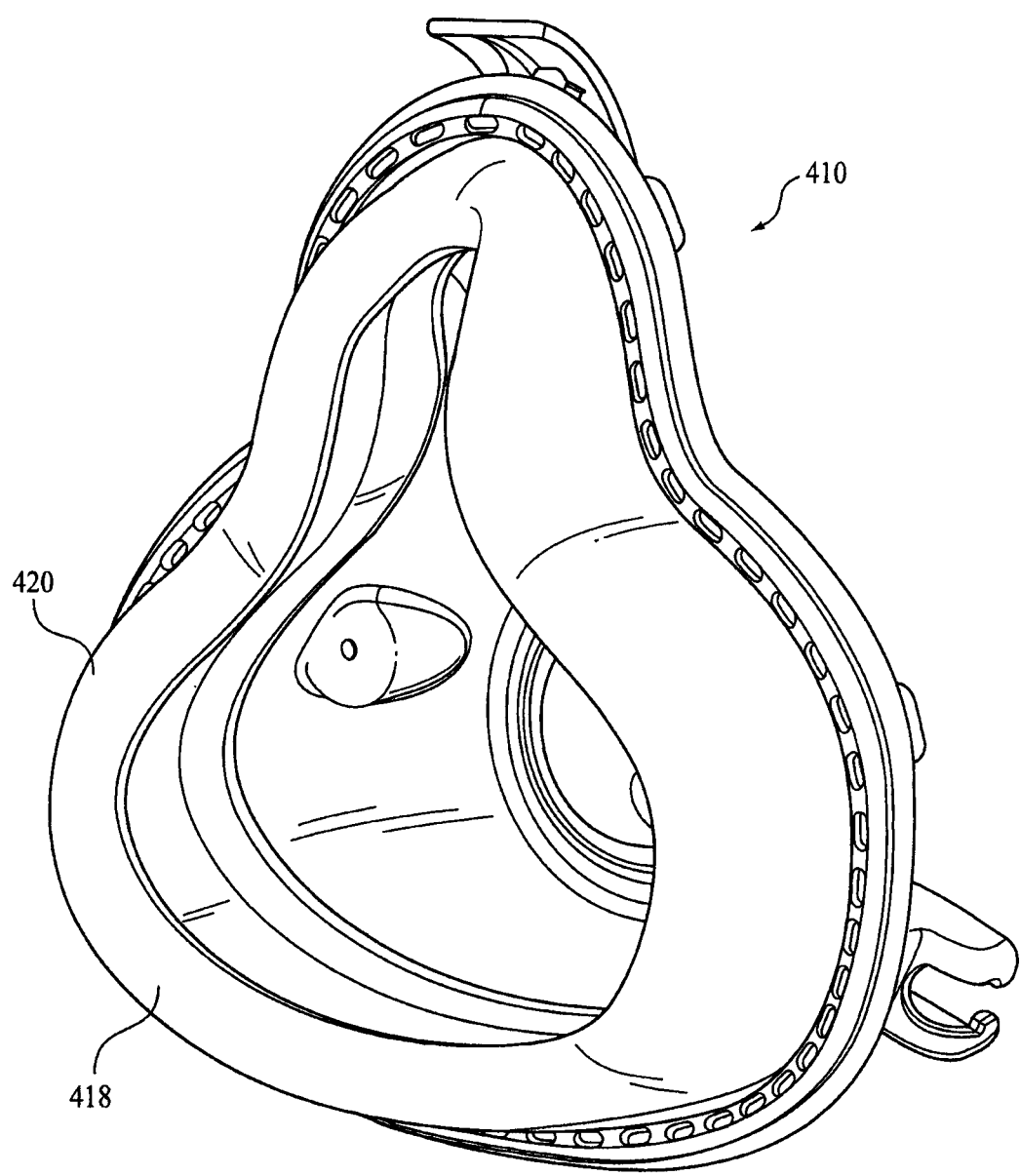
FIG. 13 perspective view of a respiratory mask according to a further embodiment of the present invention.
Figure 14:
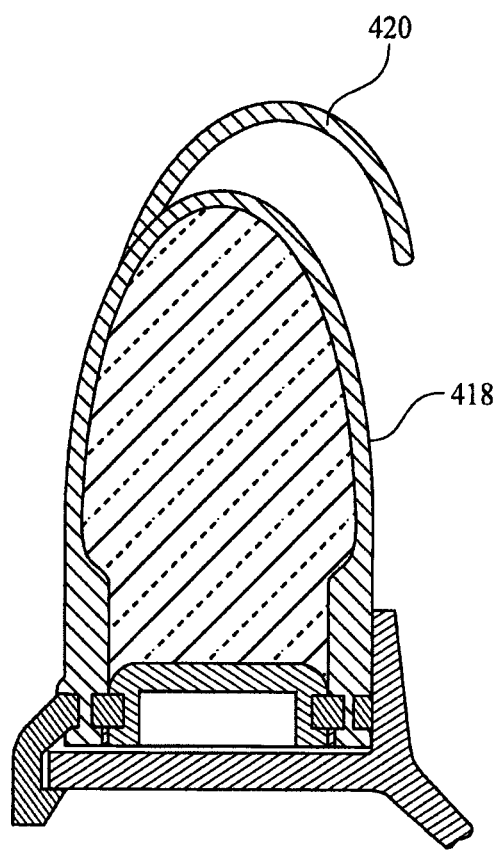
FIG. 14 is a sectional view of the seal of FIG. 13.

Another alternative embodiment of a mask 410 is shown in FIGS. 13-14. In this embodiment, seal 418 has a sealing flap 420. Sealing flap 420 is preferably made out of a very thin elastic membrane such as a silicone or TPE material. Mask 410 further includes a gel support formed as described previously. The combination of the sealing flap and the gel support enhance the seal and comfort of the mask. An air buffer like a balloon is formed between the flap and the support. Flap 420 preferably conforms to the patient's contour when it is pressurized. Flap 420 is preferably integrated in the casing as a unitary part.

In another alternative embodiment of the present invention, masks, such as those shown in the figures of the present invention, may include customizable seals such as those disclosed in U.S. Pat. Nos. 6,397,847 and 6,895,965. In one exemplary embodiment, the seal includes a formable portion adapted to be molded from a first pattern into a second pattern and to retain the second pattern responsive to being so molded. In one exemplary embodiment, a stiffening agent such as ethyl vinyl acetate is added to the super soft gel substance described above to form the formable portion.

While the presently preferred embodiments of the seal, and, in particular, the seal, have been discussed above with respect to its use on a respiratory facial mask, it is to be understood that there are a wide variety of alternative uses for the seal of the present invention. For example, the present invention contemplates using the soft gel substance enclosed by an elastic casing of the present invention as a forehead pad or for other padding, spacing, and buffering devices not limited to the face.

It should be further understood that the above described alternative embodiments of the present invention are not intended to be an exhaustive list of all of the possible uses for the seal of the present invention. In general, the seal of the present invention can be used in any situation where there is an interface between a user and an external device. It should be noted that the term "seal" is intended to encompass any interface between a patient and an external device. The term "seal" should not be construed narrowly, for example, to cover only those situations where the seal prevents foreign matter, such as water or gas, from passing to the user, e.g., a water-tight seal or an air-tight seal. It is not necessary in all embodiments of the present invention that the seal prevent matter from passing to the user. For example, if the seal of the present invention is used as an earpiece for a telephone receiver, it is not necessary that the interface between the receiver and the user provided by the seal be airtight or watertight.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A respiratory seal adapted for confronting engagement with a surface of a user to form an interface therewith, the seal comprising:
   an elastic casing having an interior chamber, wherein the elastic casing has a minimum elongation of about 400% and a hardness of about 15 to 40 Shore A, and wherein the elastic casing has a patient contacting wall thickness of about 0.008 inches to 0.025 inches (0.20 to 0.64 mm); and
   a gel substance disposed within the interior chamber, the gel substance having a cone penetration of between about 5 to 200 penetrations, wherein the elastic casing includes a base having at least one opening; and
   wherein the at least one opening is sealed by a cap having a base portion and a central wall extending upwardly from the base portion, the central wall having at least one window extending completely therethrough and structured to permit the gel substance or an adhesive to flow for mechanical bonding purposes.

\* \* \* \* \*